United States Patent
Bessler et al.

(10) Patent No.: US 11,813,389 B2
(45) Date of Patent: Nov. 14, 2023

(54) DEVICE AND METHOD FOR DEGASSING OF DIALYSIS CONCENTRATES FOR AUTOMATIC DENSITY MEASUREMENT IN MIXING INSTALLATIONS

(71) Applicant: VIVONIC GMBH, Sailauf (DE)

(72) Inventors: Patrick Bessler, Erlebenbach (DE); Stefan Eberlein, Hochberg (DE); Andreas Hemm, Alzenau (DE)

(73) Assignee: VIVONIC GMBH, Sailauf (DE)

( * ) Notice: Subject to any disclaimer, the term of this patent is extended or adjusted under 35 U.S.C. 154(b) by 213 days.

(21) Appl. No.: 16/754,146

(22) PCT Filed: Oct. 12, 2018

(86) PCT No.: PCT/EP2018/077814
§ 371 (c)(1),
(2) Date: Apr. 7, 2020

(87) PCT Pub. No.: WO2019/073017
PCT Pub. Date: Apr. 18, 2019

(65) Prior Publication Data
US 2020/0330670 A1    Oct. 22, 2020

(30) Foreign Application Priority Data

Oct. 12, 2017  (DE) .................... 10 2017 218 209.1

(51) Int. Cl.
*A61M 1/16* (2006.01)
*A61M 1/36* (2006.01)
*B01D 19/00* (2006.01)

(52) U.S. Cl.
CPC ........ *A61M 1/1658* (2013.01); *A61M 1/1666* (2014.02); *A61M 1/3627* (2013.01); *B01D 19/0063* (2013.01)

(58) Field of Classification Search
CPC .............. A61M 1/1658; A61M 1/1666; A61M 1/3627; B01D 19/0063; G01N 9/36
See application file for complete search history.

(56) References Cited

U.S. PATENT DOCUMENTS 3,827,561 A     8/1974  Serfass et al.
4,293,409 A  *  10/1981 Riede .................. A61M 1/1664
                                                210/321.71

(Continued)

FOREIGN PATENT DOCUMENTS

DE       3214635 A1    11/1982
DE       4027531 C1     7/1991

(Continued)

OTHER PUBLICATIONS

International Preliminary Report on Patentability issued in corresponding International Patent Application No. PCT/EP2018/077814 (English translation) dated Apr. 14, 2020 (11 pages).

(Continued)

*Primary Examiner* — Dirk R Bass
(74) *Attorney, Agent, or Firm* — Kilyk & Bowersox, P.L.L.C.

(57) ABSTRACT

The invention relates to a device (10) for degassing dialysis concentrates for automatic density measurement in mixing systems, comprising: an overflowable filter element (53), wherein the overflowable filter element (53) converts gas bubble-laden dialysis concentrate at the input end into a gas bubble-free dialysis concentrate at the output end. The invention also relates to a mixing system (M) having a device (10) according to the invention and a method for degassing dialysis concentrates for automatic density measurement in mixing systems (M), comprising the steps: Introducing (100) the dialysis concentrate laden with gas bubbles into the overflowable filter element (53), Filtering (Continued)

out (200) gases, Diverting (300) the gas bubble-free dialysis concentrate, Measuring (400) the density of the gas bubble-free dialysis concentrate.

10 Claims, 8 Drawing Sheets

(56) References Cited

U.S. PATENT DOCUMENTS

| | | | | |
|---|---|---|---|---|
| 2005/0284815 | A1* | 12/2005 | Sparks | A61M 1/1647 604/4.01 |
| 2010/0030151 | A1* | 2/2010 | Kirsch | A61M 1/3627 604/126 |
| 2012/0265117 | A1* | 10/2012 | Fava | A61M 1/3629 604/6.09 |
| 2016/0303305 | A1 | 10/2016 | Burbank et al. | |

FOREIGN PATENT DOCUMENTS

| | | |
|---|---|---|
| RU | 2310477 C2 | 11/2007 |
| WO | 2016104761 A1 | 6/2016 |

OTHER PUBLICATIONS

International Search Report and Written Opinion issued in corresponding International Patent Application No. PCT/EP2018/077814 (with English translation of International Search Report) dated Feb. 5, 2019 (18 pages).

Office Action issued in corresponding German Patent Application No. 10 2017 218 209.1 dated May 14, 2018 (8 pages).

Office Action and Search Report issued in corresponding Russian Patent Application No. 2020115545/14(025618) dated Feb. 8, 2022.

* cited by examiner

DEVICE AND METHOD FOR DEGASSING OF DIALYSIS CONCENTRATES FOR AUTOMATIC DENSITY MEASUREMENT IN MIXING INSTALLATIONS

This application is a National Stage Application of PCT/EP2018/077814, filed Oct. 12, 2018, which claims priority to German Patent Application No. 10 2017 218 209.1, filed Oct. 12, 2017.

The invention relates to a device and a method for degassing dialysis concentrates for automatic measurement of the density in mixing systems

BACKGROUND

In many fields of medical technology, liquid solutions having a predetermined composition are required. These liquid solutions are frequently produced on-site.

For example, dialysis fluid for dialysis is prepared by adding dialysis concentrates to purified water. The purified water is often purified by membrane filtration in a reverse osmosis system. Purified water is therefore referred to as permeate. In the majority of dialysis treatments, an acidic liquid concentrate (A concentrate) and a basic liquid concentration (B concentrate) are diluted with the permeate, wherein the A concentrate usually consists of an acidic component, dissolved salts and glucose, and the B concentrate usually consists of dissolved sodium bicarbonate.

In preparing the dialysis concentrates, in particular for the A concentrates, the methods used are those in which large drums of material in a dry or slurried form are first dissolved with purified water and/or permeate, so that they can then be processed in a dialysis machine together with additional permeate and the B concentrate to yield ready-to-use dialysis liquid at the location of treatment of the patient.

In preparation of the dialysis concentrates, the process of dissolving the substances to be dissolved is usually monitored by measuring the density. Other measurements relating to concentration may also be used, such as ion-selective measurements or laboratory analyses, for example.

However, it is found that in particular with central preparation of large quantities of dialysis concentrate, gas bubbles are frequently formed due to the process and/or large quantities of gas bubbles are introduced into the prepared concentrate. This may be caused by dissolving processes and/or by the mechanical mixing operation per se. These gas bubbles cause falsification of measurements, so that the actual density of the substance mixture is not measured.

It would be possible in principle to allow a dialysis concentrate that has been prepared to rest and to wait for the outgassing to take place naturally, but this is not feasible because of the amount of time required (up to several hours) since dialysis concentrates are generally used promptly after being prepared, so as not to have a negative effect on the planning for a smooth sequence of treatments in a dialysis center. Furthermore, there is no generally valid rule for when (almost) complete degassing can be expected with various mixtures.

It would also be desirable if not only the mixture of the end product but also the ongoing mixing operation could be monitored, for example, for the purpose of process control to the extent that a measurement error caused by gas bubbles is reduced and/or prevented.

OBJECT

The object of the invention is therefore to provide a device, which will permit a prompt measurement with a reduced error due to gas bubbles.

BRIEF DESCRIPTION OF THE INVENTION

This object is achieved by a device for degassing dialysis concentrates for automatic density measurement in mixing systems. The device has an overflowable filter element, such that the overflowable filter element converts a gas bubble-laden dialysis concentrate at the input end into a gas bubble-free dialysis concentrate at the output end, i.e., the overflowable filter element allows a prompt measurement which also enables monitoring during production. The term gas bubble-free is understood to refer to any reduction in the gas bubble content which allows an adequate reduction in the gas bubble content within the context of the following density measurement. The device for degassing dialysis concentrates for automatic density measurement can easily be integrated into existing mixing systems.

In one specific embodiment of the invention, another filter element for removing contaminants is arranged upstream from the overflowable filter element. The additional filter element may be part of the device for degassing dialysis concentrates for automatic density measurement in mixing systems as well as being part of a mixing system.

Thus the filter element can be protected from interfering substances such as undissolved salts.

In one specific embodiment of the invention, gas which is filtered through the overflowable filter element can be removed by means of an overflow, i.e., collected gas from the gas bubbles can easily be removed from the filter.

This object is also achieved by a mixing system, which makes available a device according to the invention for degassing dialysis concentrates for automatic density measurement in mixing systems, i.e., a prompt measurement which also permits monitoring during production is allowed by means of the mixing system with the overflowable filter element.

In one specific embodiment of the invention, the gas bubble-free dialysis concentrate is sent to a density measuring device. The term density measurement is understood within the scope of the invention to refer to all types of measurement which allow an inference regarding the composition of the dialysis concentrate, i.e., whether the desired dissolution of the starting substances has been achieved. This also includes the measurement of individual constituents which are representative for the entire dissolution because the other constituents have, for example, a proportional concentration and dissolving rate. Those skilled in the art are familiar with numerous measurement methods for these measurements such as methods performed with the help of ultrasound, optical or electrical signals.

In another specific embodiment of the invention, the gas bubble-free dialysis concentrate is again made available to the mixing process after the measurement, i.e., the total amount of dialysis concentrate prepared for the treatment of a human or animal does not change as a result of recycling the measured dialysis concentrate and in particular no dialysis concentrate is discarded.

In one specific embodiment of the invention, the mixing system has a mechanical mixing device.

In another specific embodiment of the invention, the mixing system and/or the device for degassing dialysis concentrates for automatic density measurement in mixing systems also has/have valves for regulating the flow through the overflowable filter element, i.e., the inflow and/or outflow can be regulated by the valves, so that the filter element is used only as needed.

In accordance with another specific embodiment of the invention, at least one of the valves that regulates the flow through the overflowable filter element is controlled in clocked fashion.

In another specific embodiment of the invention, the mixing system additionally has valves to prevent a backflow through the overflowable filter element.

A certain direction can be predetermined by means of the non-return valves. It is possible in this way to prevent a backflow of gas bubbles, for example.

The device and the mixing system according to the invention are also characterized in that the newly added components can be rinsed, and therefore cleaning, rinsing and disinfection processes can still be carried out easily.

This object is also achieved by a method for degassing dialysis concentrates for automatic density measurement in mixing systems. This method has a step of introducing the gas bubble-laden dialysis concentrate on which the measurement is to be performed into the overflowable filter element, a step of filtering out gases, a step of diverting the gas bubble-free dialysis concentrate and the step of measuring the density of the gas bubble-free concentrate, i.e., a prompt measurement is allowed by means of this method, which also permits monitoring during production or a subsequent dosing of permeate (solvent) to obtain the required amount.

In one specific embodiment of the invention, the density of a reference liquid is measured before the actual measurement.

Thus a reference value is available with which the functional suitability of the measurement device can be tested.

In another specific embodiment of the invention, the density of a reference liquid is subsequently measured to determine the density of the gas bubble-free dialysis concentrate.

Thus a reference value is available after the measurement, with which the functional capacity of the measurement device can be tested.

The reference liquid may also be embodied as a rinsing solution so that the filter is also cleaned as well as the measurement device.

Additional advantageous embodiments are the subject matter of the dependent claims and the detailed description.

BRIEF DESCRIPTION OF THE FIGURES

The invention is described in greater detail below with reference to the specific embodiments illustrated in the figures as examples, in which.

DETAILED DESCRIPTION

The invention is described in greater detail below with reference to the figures. It should be pointed out that various aspects are described which may be used either individually or in any combination, i.e., any aspect can be used with different specific embodiments of the invention unless it is presented explicitly as a mere alternative.

In addition, for the sake of simplicity reference is usually always made below to only one entity. Unless noted explicitly to the contrary, however, the invention may also comprise a plurality of such entities. To this extent the use of the words "a," "an" and "one" is to be understood only as a reference to the fact that at least one entity is used in a single specific embodiment.

Figure 1:
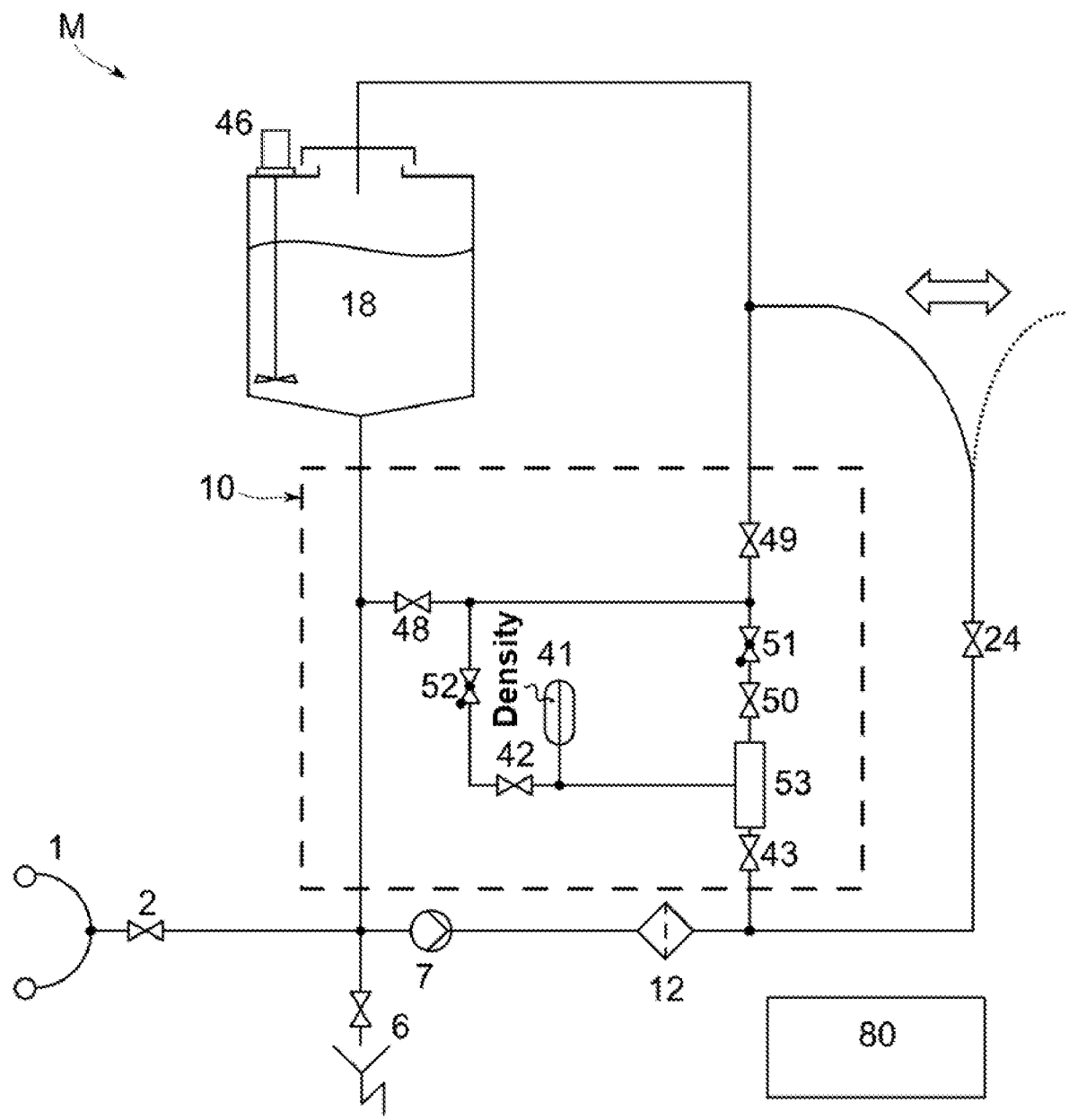
FIG. 1 shows a first schematic diagram according to specific embodiments of the invention.

In the mixing system M shown in FIG. 1, permeate is added to a mixing container 18 by means of permeate inflow 1. The inflow can be controlled by means of a valve 2, for example. In addition, a raw concentrate may be added to the mixing container. The raw concentrate is present in dry form, for example, or as a slurry and/or liquid components. The undissolved components may be present in the form of a powder or granules with or without a solid crystal structure.

The mixing and/or preparation of the dialysis concentrate may take place by means of any mixing method (e.g., beater 46) in the mixing container 18.

This involves an input of gas bubbles into the dialysis concentrate due to the process itself.

These bubbles would falsify the density measurement during quality control and therefore the gas bubbles should be removed prior to the measurement. To do so the device 10 according to the invention is used.

A device 10 according to the invention for degassing dialysis concentrates for the automatic density measurement in mixing systems M is illustrated in FIG. 1 inside the border represented by a dashed line. The device 10 has an overflowable filter element 53, such that the overflowable filter element 53 at the input end (coming out of valve 43) converts a dialysis concentrate loaded with gas bubbles into a dialysis concentrate free of gas bubbles at the output end (direction of valve 42).

Figure 5:
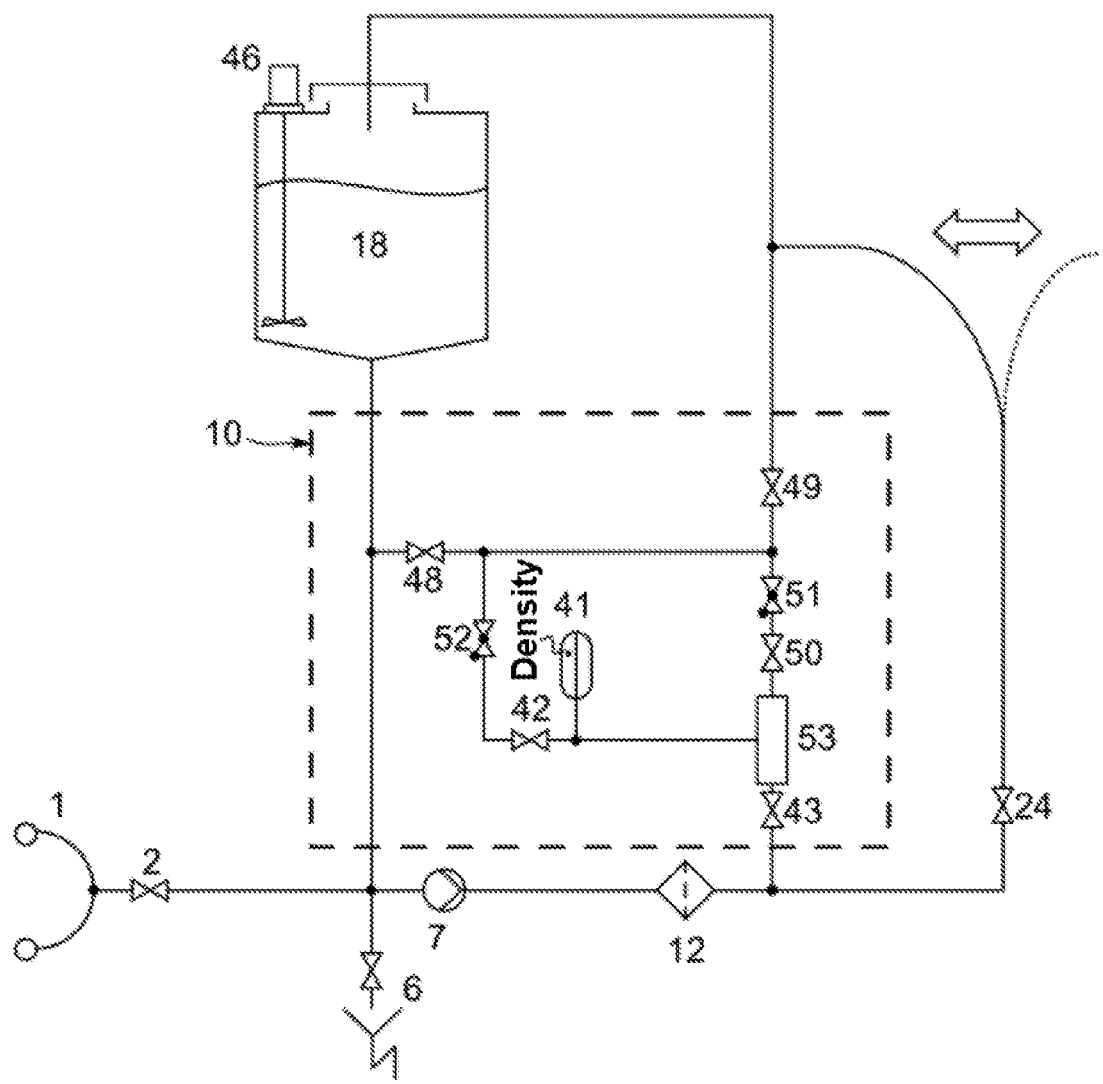
FIG. 5 shows a fifth schematic diagram according to specific embodiments of the invention.

The variant shown in FIG. 5 of the device 10 according to the invention for degassing dialysis concentrates for automatic density measurement is embodied such that it only has to be connected at precisely three points in order to be integrated functionally.

The device is connectable by means of one line to a line of the mixing system which leads from the mixing container 18 to the line node point, where lines to the valve 2 on the permeate inflow side, to the valve 6 on the outflow side, and to the pump 7, which may be arranged between the permeate inflow and the (optional) further filter element 12 for removing contaminants, converge.

The device 10 according to the invention is connectable by means of a further line on the other side of the (optional) further filter element 12 for removing contaminants.

The device 10 according to the invention is connectable by means of a further line to the line of the mixing system which leads upwardly from the mixing/withdrawal valve 24 into the mixing container 18. A valve 43, 48, 49 may be arranged in the vicinity of each of the points where the three lines of the device are connectable to the mixing system.

Embodiments which have these three valves are characterized particularly advantageously by a high level of flexibility: These embodiments of the device 10 according to the invention can be particularly easily separated from a mixing system or connected to a mixing system because they have valves in the connection region. In addition, the use of the optional valves 48, 49, which are arranged in the device 10 according to the invention in the vicinity of the connection points close to the mixing container 18 and between the mixing/withdrawal valve 24 and the mixing container, allows a coordinated control of the liquid flow. Different flow paths can thus be used particularly advantageously for different operating modes. For example, venting operation can be implemented via the valve 49 between the mixing/withdrawal valve 24 and the mixing container 18, and measurement operation can be implemented via the valve between the mixing container 18 and the pump 7.

This embodiment is particularly advantageous in that it has a high level of flexibility in respect of connections and operating modes.

Furthermore, maintenance and servicing are particularly advantageously facilitated because the device 10 according to the invention can be hydraulically separated from the mixing system.

Variants of these embodiments in which one of the two valves is omitted because the line branch in which they would be arranged is omitted are conceivable.

Figure 2:
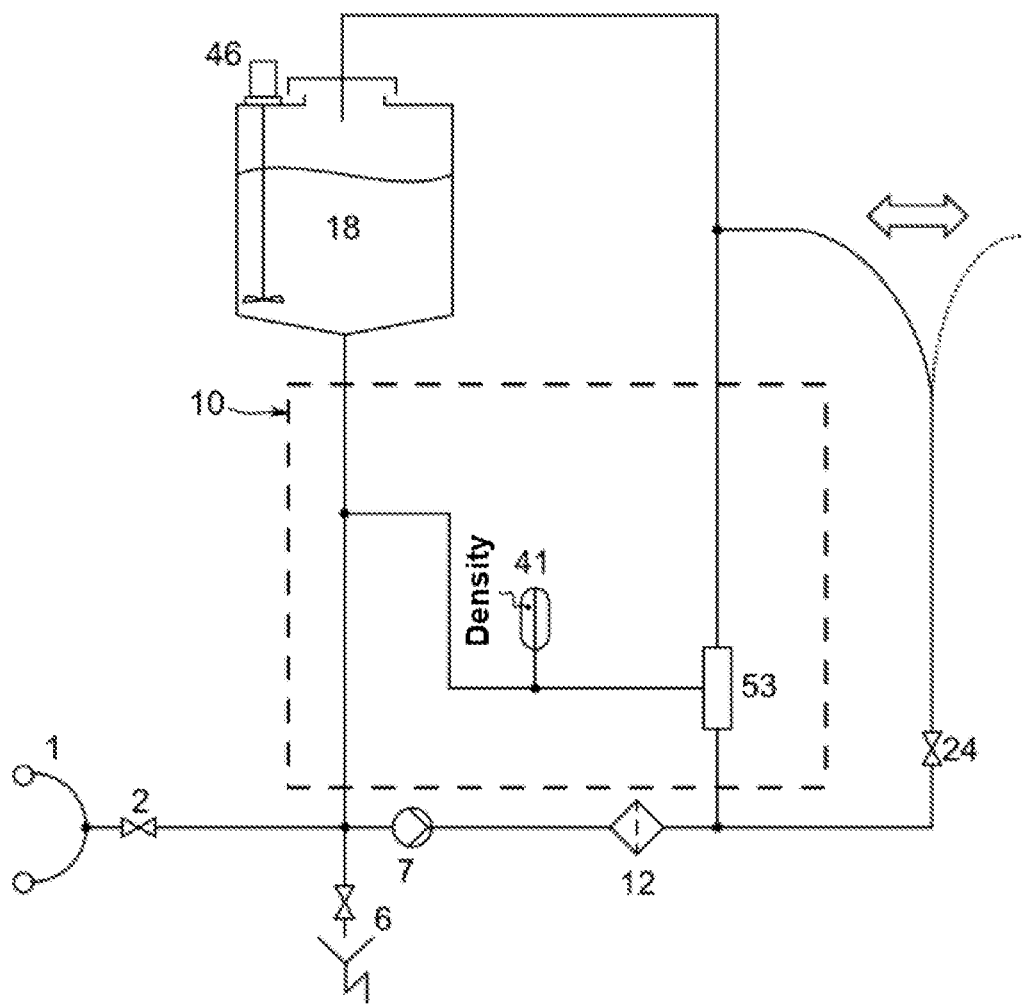
FIG. 2 shows a second schematic diagram according to specific embodiments of the invention.

The variant shown in FIG. 2 of the device 10 according to the invention for degassing dialysis concentrates for automatic density measurement in mixing systems is embodied such that, in the context of a mixing system shown in FIG. 1, it only has to be connected to precisely three points in order to be integrated functionally.

The device 10 according to the invention is connectable by means of one line to a line of the mixing system which leads from the mixing container 18 to the line node point, where lines to the valve 2 on the permeate inflow side, to the valve 6 on the outflow side, and to the pump 7, which may be arranged between the permeate inflow and the (optional) further filter element 12 for removing contaminants, converge. The density measuring device 41 is connected to this line.

The device 10 according to the invention is connectable by means of a further line on the other side of the (optional) further filter element 12 for removing contaminants.

The device 10 according to the invention is connectable by means of a further line to the line of the mixing system which leads upwardly from the mixing/withdrawal valve 24 into the mixing container 18.

The three above-described lines of the device are connected to the overflowable filter element 53.

In a minimal embodiment the device 10 according to the invention for degassing dialysis concentrates for automatic density measurement thus comprises only the following elements: The overflowable filter element 53, the density measuring device 41, and three lines.

Other embodiments may comprise further elements, starting from this minimal embodiment.

The embodiment according to FIG. 2 is preferred because it requires a small number of lines and components. It is furthermore advantageous that the liquid degassed by the overflowable filter element is fed back into the mixing system after the measurement on the intake side of the pump 7. As a result of this arrangement, a pressure difference is advantageously achieved between the primary side and the secondary side of the overflowable filter element, and in addition a flow of the liquid via the density measuring device 41 is ensured. With a suitable design of line cross-sections of the hydraulic lines it is possible to adapt the device to the mixing system such that operation when the mixing/withdrawal valve 24 is opened or closed is possible.

This embodiment is particularly advantageous in that it has a simple structure and undesirable air bubbles are removed very effectively.

Figure 3:
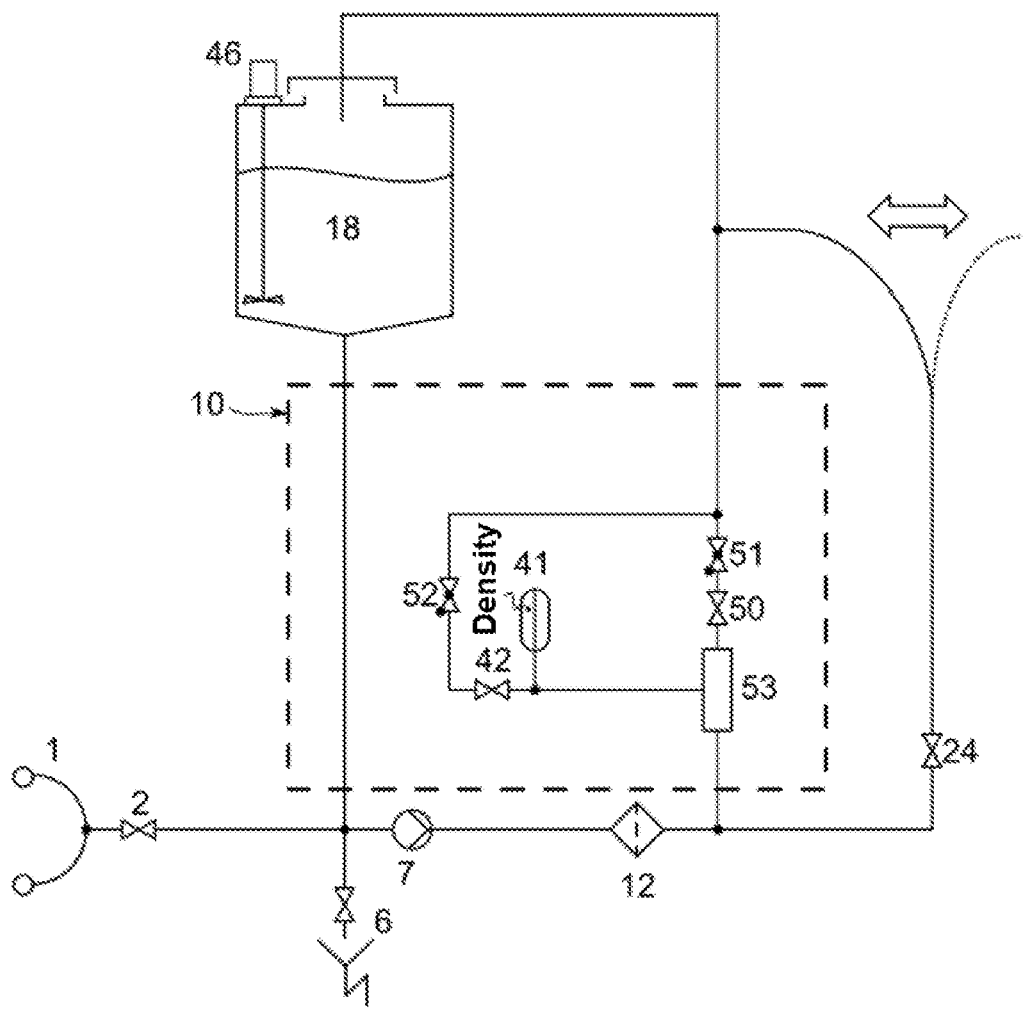
FIG. 3 shows a third schematic diagram according to specific embodiments of the invention.

In a further preferred embodiment according to FIG. 3 a device 10 according to the invention for degassing dialysis concentrates for automatic density measurement in mixing systems is embodied such that, in the context of a mixing system shown in FIG. 1, it only has to be connected to precisely two points in order to be functionally integrated.

The device 10 according to the invention is connectable by means of one line to a line of the mixing system which is attached on the side of the (optional) further filter element 12 for removing contaminants furthest from the pump 7. This line is connected to the overflowable filter element 53, to which there are attached two further lines. One of these two further lines of the device 10 according to the invention for degassing dialysis concentrates for automatic density measurements is attached, as mentioned, to an overflowable filter element 53 and is connectable at the other end to the line of the mixing system, which leads (from above) from the mixing/withdrawal valve 24 into the mixing container 18. A valve 50 and/or a non-return valve 51 or a throttle 51 may optionally be incorporated in this line.

The second further lines leads from the overflowable filter element 53 via the density measuring device 41 to the first further line, wherein the connection point is selected such that the optionally provided elements (valve 50 and/or non-return valve 51 or throttle 51) are situated between the connection point and the overflowable filter element 53. In the second further line of the device 10 according to the invention, a further valve 42 and/or a further non-return valve 52 or a throttle 52 may be arranged between the density measuring device 41 and the connection point.

To summarize, this preferred embodiment according to FIG. 3 of the device 10 according to the invention for degassing dialysis concentrates for automatic density measurement in mixing systems is embodied such that it is connectable parallel to the mixing/withdrawal valve 24. This embodiment of the device 10 according to the invention may be operated advantageously when the mixing/withdrawal valve 24 is both opened and closed. The mixing/withdrawal valve 24 may advantageously be held closed during the venting of the overflowable filter element 53. A particularly high liquid flow may thus be conducted particularly advantageously through the filter element 53 and the line by the valve 50 and non-return valve 51 or throttle 51. Undesired gas accumulations, for example air, can be rinsed out from these elements particularly advantageously by the high flow.

The liquid flows via the primary and secondary side of the filter element 53 can be controlled particularly advantageously by means of the optional valves 42, 50. This controllability is particularly advantageous in the case of the venting of the device for degassing dialysis concentrates for automatic density measurement in mixing systems.

Alternatively the optional valves 42, 50 can be controlled in clocked fashion. The optional non-return valves 51, 52 or throttles 51, 52 may be spring-loaded advantageously and may prevent a backflow and also enable the setting of different liquid pressures on the primary and secondary side of the filter. The liquid flows may thus advantageously be controlled continuously.

In the case of operation of the device 10 according to the invention with closed mixing/withdrawal valve 24, the optional non-return valves 51, 52 or throttles 51, 52 may advantageously be embodied as static throttles.

This embodiment particularly advantageously enables a forced venting of the device. In addition, this embodiment of the device 10 according to the invention particularly advantageously enables the targeted control of liquid flows for various operating modes of the device and/or the mixing system, such as measurement operation, rinsing operation, or disinfection operation. This embodiment is particularly advantageous in that it has a simple structure and removes undesirable air bubbles very effectively.

Figure 4:
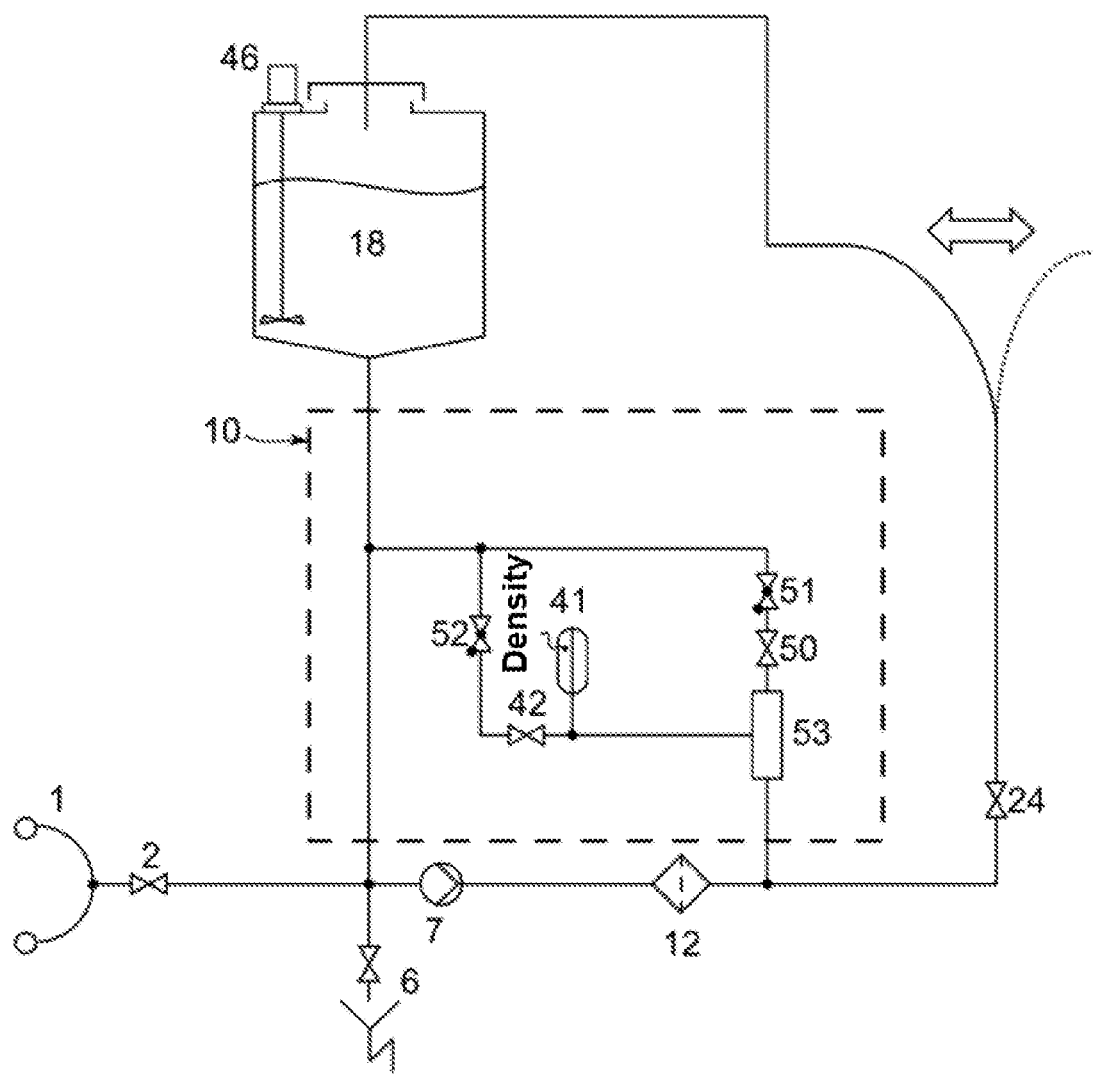
FIG. 4 shows a fourth schematic diagram according to specific embodiments of the invention.

In a further preferred embodiment according to FIG. 4 a device 10 according to the invention for degassing dialysis concentrates for automatic density measurement in mixing systems are embodied such that, in the context of a mixing system shown in FIG. 1, it only has to be connected to precisely two points in order to be integrated functionally.

The device is connectable by means of one line to a line which is attached on the side of the (optional) further filter element (12) for removing contaminants furthest from the pump 7. This line is connected to the overflowable filter element 53, to which two further lines are attached.

The device is connectable by means of a further line to a line of the mixing system which leads from the mixing container 18 to the line node point where lines to the valve 2 on the permeate side, to the valve 6 on the outflow side, and to the pump 7, which is arranged between the permeate inflow and the (optional) further filter element 12 for removing contaminants, converge. The density measuring device 41 is connected to this line of the device 10 according to the invention. Between this end of the device 10 according to the invention and the filter element 53, the device 10 according to the invention is characterized by two parallel line branches. In one branch there are optionally situated a valve 50 and/or a non-return valve 51 or a throttle 51. The other branch leads from the overflowable filter element 53 via the density measuring device 41 to an optional further valve 42 and/or an optional further non-return valve 52 or throttle 52.

In this embodiment the output of the device 10 according to the invention is connectable to the intake line of the pump 7 of the mixing system. Consequently, during subsequent operation and when the mixing/withdrawal valve 24 is open, the device 10 according to the invention can be operated with lower liquid flows than in other embodiments of the device 10 according to the invention for degassing dialysis concentrates for automatic density measurement in mixing systems. The flows are much higher when the mixing/withdrawal valve 24 is closed.

The liquid flows via the primary and secondary side of the overflowable filter element 53 can be controlled particularly advantageously by means of the optional valves 42, 50. This controllability is particularly advantageous in the case of the venting of the device 10 according to the invention for degassing dialysis concentrates for automatic density measurement in mixing systems.

Alternatively, the optional valves 42, 50 can be controlled in clocked fashion. The optional non-return valves 51, 52 or throttles 51, 52 may advantageously be spring-loaded, and in this embodiment are used primarily for flow regulation, since the low pressure on the intake side of the pump 7 already prevents a backflow.

This embodiment can be operated particularly advantageously at low flow rates when the mixing/withdrawal valve 24 is open.

In this embodiment the relatively lower pressure on the intake side of the pump 7 particularly advantageously prevents a backflow of the conveyed liquids.

A forced rinsing is particularly advantageously possible with this embodiment.

This embodiment of the device according to the invention additionally particularly advantageously enables the targeted control of liquid flows for various operating modes of the device 10 according to the invention and/or the mixing system, for example measurement operation, rinsing operation, or disinfection operation. In this embodiment it should be considered that gas bubbles, for example air, could be guided back to the pump.

Figure 6:
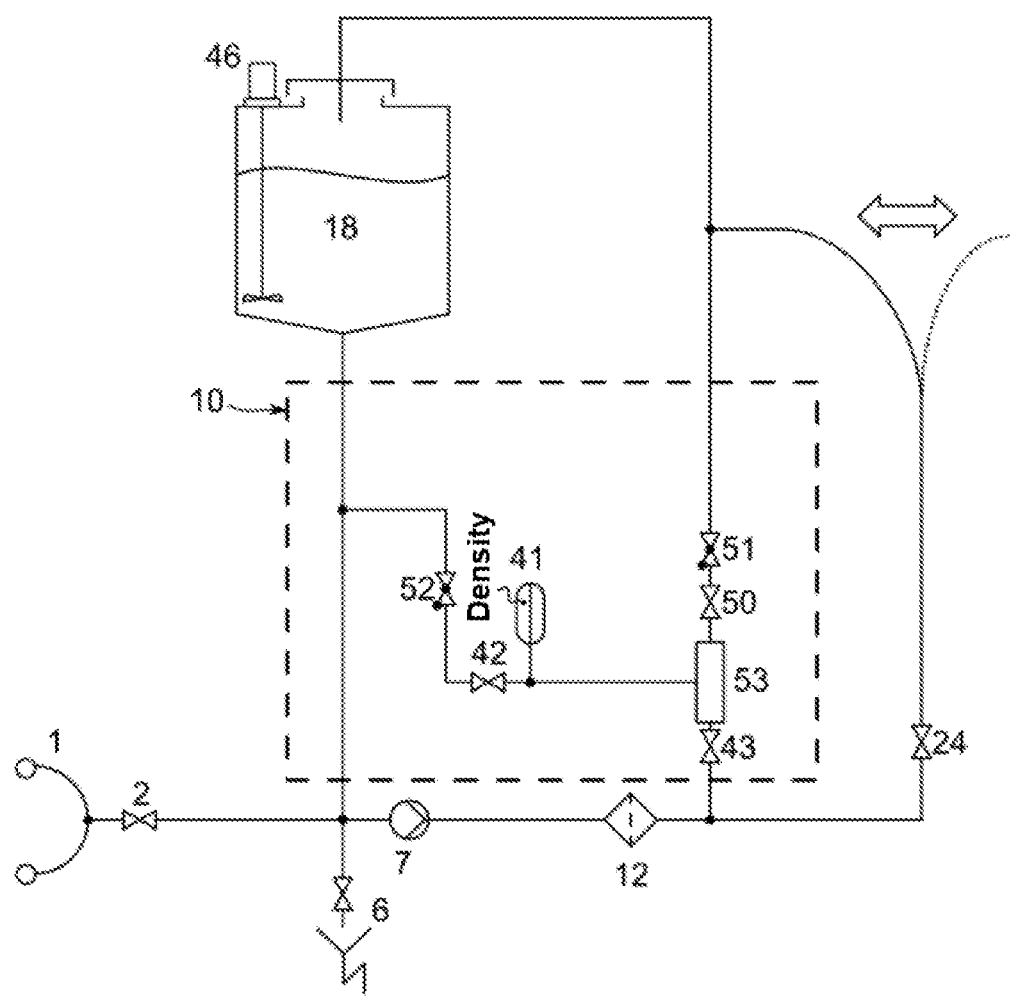
FIG. 6 shows a sixth schematic diagram according to specific embodiments of the invention.

In a further preferred embodiment according to FIG. 6 a device according to the invention for degassing dialysis concentrates for automatic density measurement in mixing systems is embodied such that, in the context of a mixing system shown in FIG. 1, it only has to be connected to precisely three points in order to be integrated functionally.

The device is connectable by means of one line to a line of the mixing system which leads from the mixing container 18 to the line node point, where lines to the valve 2 on the permeate inflow side, to the valve 6 on the outflow side, and to the pump 7, which is arranged between the permeate inflow and the (optional) further filter element 12 for removing contaminants, converge. In the device according to the invention this line is connected to the overflowable filter element 53, to which two further lines are attached. The density measuring device 41 is arranged in this line of the device, and a valve 42 and/or a non-return valve 52 or a throttle 52 may be arranged between the density measuring device 41 and the connection point to the mixing system.

A further line of the device 10 according to the invention for degassing dialysis concentrates for automatic density measurements attaches to the overflowable filter element 53 and is connectable at the other end to the line of the mixing system which leads (from above) from the mixing/withdrawal valve 24 into the mixing container 18. A further valve 50 and/or a further non-return valve 51 or a further throttle 51 may optionally be incorporated in this line.

The device 10 according to the invention is connectable by means of a further line to a line of the mixing system which attaches on the side of the (optional) further filter element 12 for removing contaminants furthest from the pump 7 and leads to the mixing/withdrawal valve 24. A further valve 43 may optionally be incorporated in this line of the device.

This particularly advantageous embodiment combines a number of advantages of various of the aforementioned particularly advantageous embodiments. It therefore particularly advantageously comprises a relatively simple ensemble of hydraulic flow paths, as is the case in the above-mentioned minimal embodiment.

To this end, the liquid flows via the primary and secondary side of the filter element can be controlled particularly advantageously by means of the optional valves 42, 50. This controllability enables particular advantages in the case of a forced venting or rinsing or disinfection of the lines of the device for degassing dialysis concentrates for automatic density measurement in mixing systems. In addition the use of optional valves 42, 43, 50 in the connection region between the device and the mixing system particularly advantageously enables a facilitation of the maintenance and servicing because individual flow paths through the device can be separated hydraulically from the mixing system. The optional non-return valves 51, 52 or throttles 51, 52 can advantageously be spring-loaded and prevent a backflow and also enable the setting of different liquid pressures on the primary and secondary side of the filter. The liquid flows are thus advantageously controlled continuously.

By means of the invention, it is now possible to enable a prompt measurement with reduced error due to gas bubbles. It is also possible to not only monitor the mixture as an end product but instead to also monitor the mixture in the ongoing mixing operation without resulting in a falsification of measurement results due to gas bubbles, i.e., the concentration and/or density can be measured rapidly, so that the quality and safety for patients are improved.

The overflowable filter element 53 in all variants may also consist of a plurality of parallel and/or serial filter elements—even though it is referred to below as a filter element. These filter elements may be similar or different.

In one specific embodiment of the invention, another filter element 12 is arranged upstream from the overflowable filter element 53 (in the direction of flow) for removing contaminants. The additional filter element 12 may thus be part of the device 10 for degassing dialysis concentrates for automatic density measurement in mixing systems as well as being part of a mixing system M.

Thus, the overflowable filter element 53 can be protected from disturbing substances such as dirt, particles of raw materials, undissolved salts, etc. This increases the functional reliability of the overflowable filter element 53.

According to specific embodiments of the invention, the gas filtered out as gas bubbles can be removed through the overflowable filter element 53 by means of an overflow in the direction of the valve 50, i.e., the gas bubbles are retained by the filter element 53 on the primary side and are rinsed off with the overflow. The gas (air bubbles) can be separated from the filter element 53 through optional valves 50 and 51 wherein no dialysis concentrate is discarded and/or none is lost because the measured medium and the medium containing gas bubbles can be combined again after the measurement and sent back to the mixing container. The gas then flows further in the direction of the mixing container 18 and exits there. Larger gas bubbles escape into the environment while smaller gas bubbles may be entrained by the fluid inflow with the dialysis concentrate which is at the bottom of the mixing container 18. However, there is no harm in this because gas bubbles can also be introduced here during normal mixing operation.

For example, the dialysis concentrate can be taken downstream from the valve 24 as indicated by the dashed line and the double arrow. To convey the dialysis concentrate or the permeate in the line system, one pump 7 or a plurality of pumps may be provided.

The device 10 may readily be used as a retrofitted element for traditional mixing systems. However, it is also possible to provide that the device 10 is already integrated into a mixing system M.

The gas bubble-free dialysis concentrate may be sent to a density measuring device 41 which is a component of the device 10 or of the mixing system M. The filtered dialysis concentrate which is available in a form in which it is free of gas bubbles on the secondary side of the overflowable filter element 53 can thus be measured without any error.

The gas bubble-free dialysis concentrate can readily be made available to the mixing process again after the measurement in a measurement instrument, for example, the density measuring device 41. Optional valves 42, 52 may be provided for this purpose. The optional valves may be controlled in clocked fashion.

In specific embodiments of the invention, the mixing system M has a mechanical mixing device 46, for example, a beater. A beater is a term that is known in general and may also be understood to be a magnetically driven stirring mechanism, for example.

According to additional specific embodiments of the invention, the mixing system M and/or the device 10 also has/have valves 42, 43, 48, 49, 50 to regulate the flow through the overflowable filter element 53. The device 10 and/or the mixing system M can also be separated from the continuous flow in this way, so that, for example, maintenance is facilitated, i.e., the device 10 can be operated in parallel with the mixing circuit. In addition, flow-reducing elements can be provided so that, for example, the flow through the overflowable filter element 53 is lower than the flow through the mixing/withdrawal valve 24.

According to other specific embodiments of the invention, the mixing system M and/or the device 10 also has/have valves 51, 52 to prevent a backflow through the filter element 53, through which the flow passes. The valves 52 and 42 as well as 51 and 50 may obviously each also be embodied as a single valve. The valves 51, 52 may be non-return valves, for example. To be able to achieve suitable flow rates, the (non-return) valves 51, 52 may be embodied with different reset forces and/or throttles (stenoses) may be used in the measurement circuit. Throttles may also be embodied as static throttles.

After mixing and transfer of the dialysis concentrate, individual, multiple or all flow paths of the mixing system M and/or of the integrated device 10 can be rinsed and/or disinfected through the valve switching 42, 43, 48, 49, 50. Liquids can be discarded through a vein (valve 6).

Figure 7:
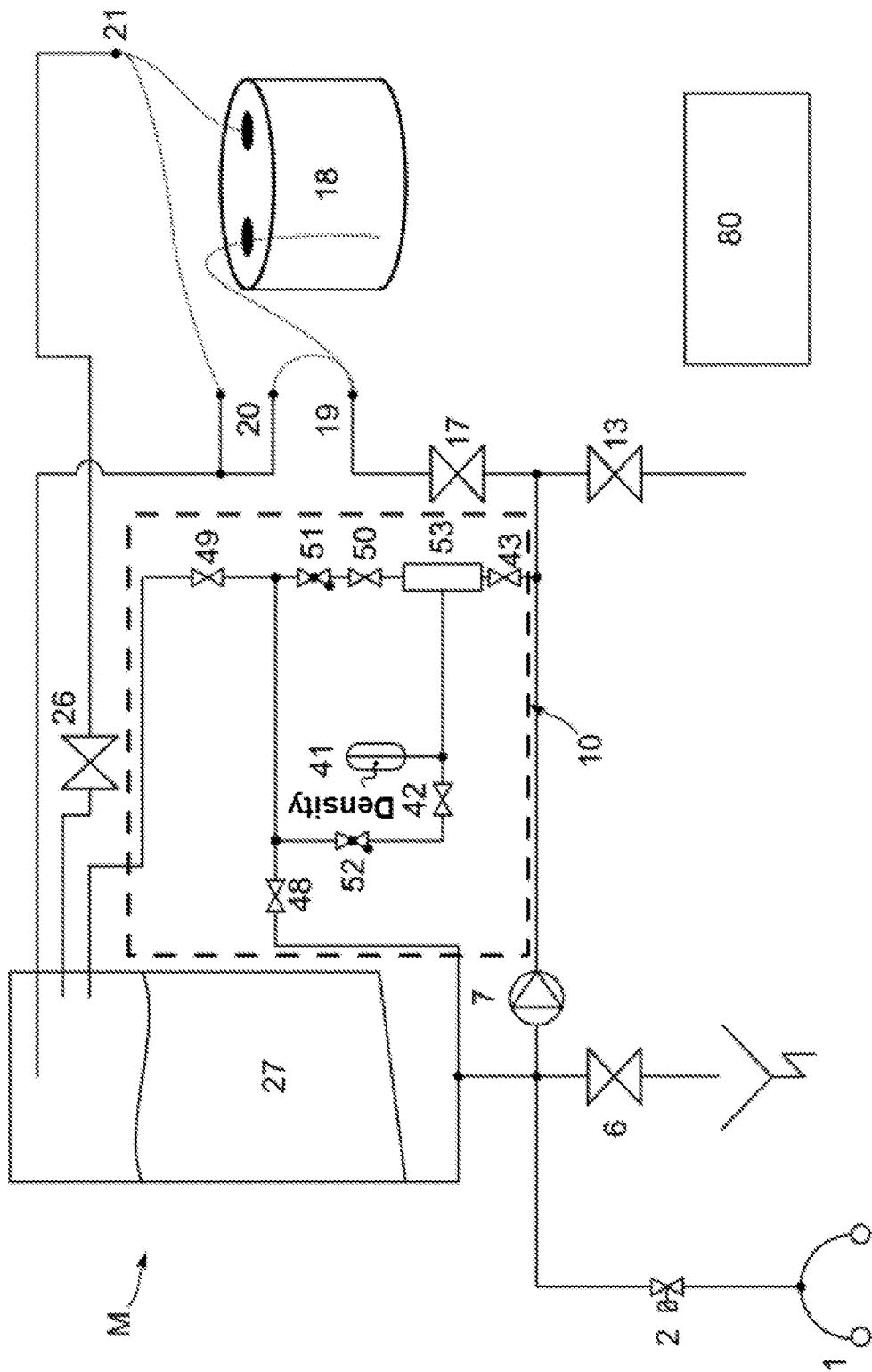
FIG. 7 shows a sixth schematic diagram according to specific embodiments of the invention.

FIG. 7 shows, in an exemplary manner for all variants, the use of a device 10 according to the invention for degassing dialysis concentrates in an alternative mixing system M. The (mixing) container 18 here is a replaceable container which need not be rinsed and may be designed as a disposable container. The disposable container is then often also referred to as a raw material container. For the mixing, permeate is added to the container 27 by means of a permeate inflow 1. The inflow can be controlled by means of a valve 2, for example. Furthermore, the container 18 is connected to the mixing system M so that the connection 19 is attached to the container 18. As a result of this connection, liquid from the container 27 is introduced into the container 18—for example, by means of the pump 7 through the valve 17. In addition, the container 18 is connected to the connection 21. Through this connection, liquid flows through the container 18 during mixing and the liquid from the container 18 is carried back through the valve 26 into the container 27. Because of this continuous flow through the container 18, the raw concentrate in the container 18 is dissolved. The flow through the container 18 causes a pressure in container 18 so that it is embodied as a pressurized container.

The finished mixed dialysis concentrate can be stored in storage containers (not shown), for example, through valve 13 (with valve 17) and made available to the dialysis machines from there.

During the mixing (for online monitoring or evaluation of the mixing progress) or after conclusion of the mixing, the density of the liquid with the raw concentrate already dissolved can be measured/tested with the device 10 (which is integrated as a bypass into the mixing system M).

After the mixing operation, the container 18 is uncoupled from the mixing system M so that the connections 19 and 21 are connected to the connection 20, as indicated in FIG. 2, during the rinsing operation. For rinsing the mixing system M, all the flow paths are rinsed with permeate and/or are disinfected with disinfectant solution for the step of disinfection. For control by means of the valve 26, either the mixing line (valve 26 open) or the mixing tank (valve 26 closed) may be rinsed/disinfected. A spray head with which the rinsing liquid and/or disinfectant solution is distributed over the tank wall is mounted in the mixing tank on the rinsing line (illustrated above valve 26). Then the container 27 is rinsed and/or disinfected. The integrated device 10 with all its flow paths can be cleaned by means of the corresponding valve circuits. After successful cleaning of the mixing system the liquid can be disposed of into the drain through the valve 6.

Figure 8:
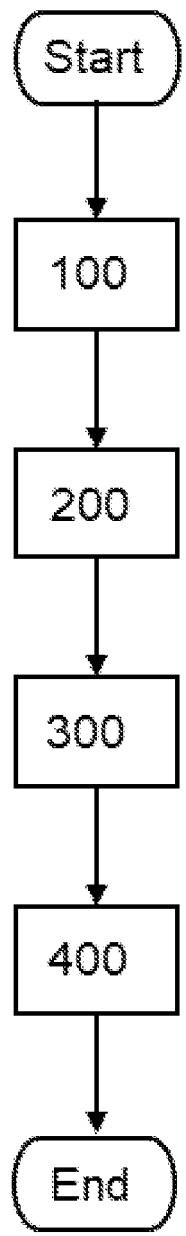
FIG. 8 shows a schematic flow chart according to specific embodiments of the invention.

The object of the invention is also achieved by a method for degassing dialysis concentrates for automatic density measurement in mixing systems M according to FIG. 8.

This method begins with the step of introducing 100 the gas bubble-laden dialysis concentrate to be measured into the overflowable filter element 53. The overflowable filter element 53 filters out gas bubbles in step 200. Then the gas bubble-free dialysis concentrate is diverted in step 300 and measured with a suitable (density) measurement device 41 in step 400.

In another specific embodiment of the method, a reference liquid is first measured with the measuring device 41 in an optional phase of the method prior to step 100. In doing so, for example, the permeate may serve as a reference liquid. Since the permeate has a certain density (and/or a certain conductivity), for example, the permeate can serve as a reference liquid.

In yet another specific embodiment of the method, the density of a reference liquid is measured in an optional method segment using the measuring device 41 after step 400. Then, for example, the permeate may serve as the reference liquid. Since the permeate has a certain density (and/or a certain conductivity), for example, the permeate can serve as the reference liquid.

The overflowable filter element 53 may readily be designed, so that the change in the measurement to be measured can be implemented rapidly and without any residues.

In addition, through appropriate settings of the valves 42, 43, 48, 49 and 50 a wide variety of flow rates can be implemented, so that, on one hand, the device 10 is easy to service and maintain but also, on the other hand, can be easily cleaned and disinfected, for example. By means of the valves 42, 43, 48, 49 and 50 it is also possible not only to regulate the direction of flow but also the flow itself through the primary and/or secondary circuit of the overflowable filter element 53.

For example, in the case of cleaning and/or disinfection, it is possible to provide that the flow-through medium is discharged through drain valve 6. The rinsing could be controlled through the measurement device 41.

With the invention presented here, a safe automatic method for prompt/simultaneous density determination on the dialysis concentrate with elimination of validation errors due to gas bubbles is made possible during an ongoing mixing operation. Waiting times, operational errors and/or inaccuracies are reduced or even prevented entirely with this method.

The function of the measurement device can be ensured by the optional method including verification of the measuring device 41 with a reference liquid prior to use for a mixing operation.

Process control is already possible during the mixing. The degree of dissolution of the added raw concentrate can be determined in this way.

A method for dilution of dialysis concentrate to certain target density values is also possible by using this method and this device.

In one specific embodiment, the mixing device M according to the invention comprises a control device 80, which is configured so that the pumps and valves are controlled by connecting lines (not shown) and the signals of the sensor 41 are read out in the same way, so that the method according to the invention can take place as a fully or partially automated process.

The invention claimed is:

1. A system that enables automatic density measurement of dialysis concentrates, the system comprising:
   a mixing system comprising
      a mixing container, and
      a mixing circuit comprising at least one mixing line that leads from the mixing container and back to the mixing container;
   a device integrated as a bypass of the mixing system, the device comprising
      an overflowable filter element comprising an input end and an output end,
      a first line that leads from the mixing system and is connected to the input end of the overflowable filter element,
      a second line connected to the output end of the overflowable filter element and leads to the mixing system, and
      a density measuring device arranged in the second line; and
   at least one pump, wherein
      the mixing system prepares the dialysis concentrates,
      the overflowable filter element converts gas bubble-laden dialysis concentrate at the input end into a gas bubble-free dialysis concentrate at the output end, and
      the at least one pump is configured to convey liquid through the mixing system and the device such that the system is capable of determining density of the gas bubble-free dialysis concentrate during ongoing preparation of the dialysis concentrate.

2. The system, according to claim 1, wherein the overflowable filter element consists of a plurality of parallel and/or serial same or different filter elements.

3. The system, according to claim 1, wherein gas filtered through the overflowable filter element is removed by an overflow.

4. The system, according to claim 1, further comprising a plurality of valves configured to regulate the flow through the overflowable filter element.

5. The system, according to claim 4, wherein at least one of the plurality of valves that regulates the flow through the overflowable filter element is controlled by a control device.

6. The system, according to claim 1, further comprising at least one valve to prevent backflow through the overflowable filter element.

7. The system, according to claim 1, wherein the second line is configured to direct the gas bubble free dialysis to the mixing system after measurement.

8. The system, according to claim 1, wherein another filter element is arranged upstream from the overflowable filter element, to remove contaminants.

9. The system, according to claim 1, wherein the mixing system has a mixing device with a mechanical or physical action.

10. The system, according to claim 1, wherein dissolution of raw material is carried out by liquid circulation through the mixing container.

\* \* \* \* \*